United States Patent [19]

Francis

[11] 4,321,932

[45] Mar. 30, 1982

[54] ELECTRODE IMPEDANCE MONITORING METHOD APPARATUS FOR ELECTROCARDIOGRAPHY

[75] Inventor: David B. Francis, Mt. Kisco, N.Y.

[73] Assignee: International Business Machines Corporation, Armonk, N.Y.

[21] Appl. No.: 53,637

[22] Filed: Jun. 29, 1979

[51] Int. Cl.³ .............................................. A61B 5/04
[52] U.S. Cl. .................................................... 128/696
[58] Field of Search ........ 128/695, 696, 734, 639–642, 128/710

[56] References Cited

U.S. PATENT DOCUMENTS 3,976,055  8/1976  Monter et al. ...................... 128/641
4,027,663  6/1977  Fischler et al. ..................... 128/710

OTHER PUBLICATIONS

"Medical Engineering", Ray, Charles D., Year Book Medical Publishers, Chicago, 1974, pp. 1011–1012.

*Primary Examiner*—William E. Kamm
*Attorney, Agent, or Firm*—Ronald L. Drumheller

[57] ABSTRACT

A patient's own heart is used as a voltage source for measurement of EKG electrode impedance. The amplitude of an EKG signal obtained while the EKG electrodes are shorted together with an impedance is compared to the amplitude of an EKG signal obtained under identical conditions except that the impedance short is not present. The value of the inter-electrode impedance is then equal to one less than the ratio between the unshorted amplitude and the shorted amplitude times the value of the shorting impedance. In a preferred embodiment, the value of the shorting impedance is made equal to the maximum permitted inter-electrode impedance. Then, if the amplitude of the EKG signal taken from a patient decreases upon temporary insertion of the impedance short to a value less than half of the EKG amplitude obtained without the impedance short, the inter-electrode impedance is too high.

23 Claims, 5 Drawing Figures

ELECTRODE IMPEDANCE MONITORING METHOD APPARATUS FOR ELECTROCARDIOGRAPHY

DESCRIPTION

1. Field of the Invention

This invention relates to electrocardiography and, more particularly, to apparatus for monitoring the impedance of EKG electrodes.

It is particularly important for correct and accurate operation of any electrocardiographic (EKG) apparatus, whether it is monitoring patient condition or collecting electrocardiogram signals, that the detected heart beat signals must be of sufficient quality. The most important requirement for high quality EKG signals is that the EKG electrode impedances must be sufficiently low. The cause of a high EKG electrode impedance is usually a high contact impedance between one or more electrodes and the patient's skin. The skin contact impedance may be high because of improper installation of the electrode or perhaps because the electrode has become partly or fully detached from the skin surface. Another possible cause of unusually high electrode impedance might be broadly called lead failure and refers to any high impedance along the electrical path from the electrode to the first amplifying stage of the EKG apparatus. Electrical connectors can produce this type of high electrode impedance. Whatever the source, a high electrode impedance results in receiving signals at the first amplifying stage which are not true or reliable representations of heart activity. It should be readily apparent that detection of EKG electrode impedances which are too high is valuable in any EKG apparatus and is particularly important in situations where the EKG signals are being merely collected and are not being immediately displayed, plotted, processed or analyzed.

In most prior art EKG apparatus, the input amplification stages have very high input impedance in order to make the EKG apparatus as insensitive as possible to variations in electrode impedance. Other attempts have been made to further reduce sensitivity to electrode impedance variations. For example, in U.S. Pat. No. 3,500,823 the EKG electrode is made purely capacitive so that there will be no sensitivity at all with respect to variations in ohmic contact resistance. This does not, however, remove sensitivity to other sources of ohmic lead resistance variation nor does it consider at all that total electrode impedance still varies with changes in the effective capacitance thereof. Direct monitoring of electrode impedance is preferable and is taught, for example, in U.S. Pat. Nos. 3,495,584 and 4,027,663. In these patents the electrode impedance is effectively placed in a feedback loop of an oscillator circuit. When the electrode impedance gets above a predetermined threshold, the oscillator changes state (it either begins oscillating or stops oscillating) and the change of state is detected and indicated to an operator in some way. In one teaching (U.S. Pat. No. 3,495,584) the frequency of oscillation is high (5 kilohertz) and in the other (U.S. Pat. No. 4,027,633) it is low (40 hertz).

In general, impedance changes as a function of frequency. It follows that the magnitude of the oscillator sensed impedance is generally dependent upon the chosen frequency of oscillation. The magnitude of this impedance, which has been sensed at a single frequency, may or may not be closely related to the effective (or average or maximum) impedance experienced by an EKG signal, which is a peculiar mix of frequency components between about 0.05 hertz and 100 hertz.

Another disadvantage of these prior art impedance monitors is that the patient must necessarily be in the oscillator feedback circuit, which means that some voltage, however small, must necessarily be applied to the patient. The oscillator waveform is actually applied to the patient. This is contrary to the present day requirement that the patient be totally isolated as much as possible from any electrical equipment. Deliberate application of voltage to a patient is always to be avoided if possible.

Still another disadvantage of such impedance monitors is that the oscillator adds a signal to the true EKG waveform. Since this added signal has a known frequency, it can be filtered from the combined waveform, but not without also filtering the same frequency component from the true EKG signal. If the oscillator frequency is not within the range of frequency components of the EKG signal, this causes no distortion of the true EKG waveform, but then the electrode impedance is being measured at a frequency which is outside the range of frequencies at which the electrode is intended to be used.

It is an object of this invention to measure and to provide apparatus for measuring EKG electrode impedance without applying any signal whatsoever to the patient and without removing the patient from otherwise total electrical isolation.

A further object is to effectively measure and to provide apparatus for measuring the EKG electrode impedance with the same mix of frequency components normally encountered by the EKG electrode during collection of EKG waveforms.

Still another object is to measure and to provide apparatus for measuring EKG electrode impedance without distorting the collected EKG waveform in any way.

It is also an object to provide a method or technique and apparatus for measuring EKG electrode impedance which can be conveniently implemented with a minimum of additional components in EKG apparatus which already contains a digital computer for EKG analysis.

DISCLOSURE OF THE INVENTION

These and further objects of the invention which will become apparent upon a reading of the specification in conjunction with the attached drawings are obtained by using the patient's own heart signals as the voltage source for measurement of EKG electrode impedance. The amplitude of an EKG signal ($A_L$) obtained while the EKG electrodes are connected together through an impedance (loaded) is compared to the amplitude ($A_U$) of an EKG signal obtained under identical conditions except that the impedance load is not present. The value of the interelectrode impedance is then equal to one less than the ratio between the unloaded amplitude $A_U$ and the loaded amplitude $A_L$ times the value of the loading impedance $Z_T$. In a preferred embodiment, the value of the loaded impedance is made equal to the maximum permitted inter-electrode impedance. Then, if the amplitude of the EKG signal taken from a patient decreases upon temporary insertion of the loading impedance to a value less than half of the EKG amplitude obtained without such loading impedance, the interelectrode impedance is too high.

BEST MODE FOR CARRYING OUT THE INVENTION

Figure 1:
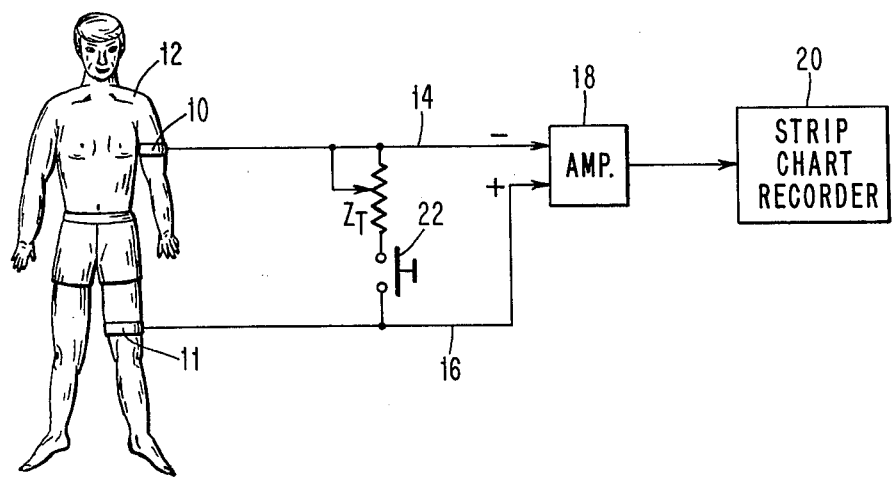
FIG. 1 schematically illustrates a manually operated simplified embodiment of this invention.

Referring now to the drawings, FIG. 1 illustrates the principles of the present invention through a manually operated embodiment thereof. An EKG sensing electrode 10 and a reference electrode 11 are attached to an arm and leg respectively of patient 12. It should be understood that in practice more than two electrodes are ordinarily attached in order to be able to record EKG waveforms at several different locations simultaneously. Although the present invention is described with respect to only two electrodes and a single EKG waveform taken therebetween, it should be apparent that the invention may be extended for use with any number of electrodes and any number of waveforms. The voltage signals at electrodes 10, 11 are conveyed by conductors 14, 16 to differential amplifier 18. Differential amplifier 18 then presents an EKG waveform to strip chart recorder 20 which is the time variation of the measured difference between the potential at electrodes 10 and 11.

A test impedance $Z_T$ is connected in series with a normally open pushbutton switch 22 between conductors 14 and 16 in order to allow test impedance $Z_T$ to be temporarily inserted as a loading impedance between conductors 14 and 16 through depression of pushbutton 22. Test impedance $Z_T$ is variable as shown so that the amount of loading placed upon the electrodes during the loading test may be varied if desired. In one mode of operation the test impedance is varied until a loading effect is noticed upon EKG signal amplitude. The value of the inter-electrode impedance may then be derived from the value of the test impedance which produced a loading effect in accordance with the formula $$Z_E = Z_T(A_U/A_L - 1)$$

where $Z_E$ is the inter-electrode impedance, $A_U$ is the unloaded amplitude of the EKG signal and $A_L$ is the loaded amplitude of the EKG signal.

The input impedance of differential amplifier 18 should be as high as possible. In order for the above-disclosed formula to be accurate, the input impedance of the differential amplifier must be so much higher than $Z_T$ that the loading effect produced by amplifier 18 may be neglected. It will be apparent that if amplifier 18 does have a significant loading effect, Ohm's Law can be used to derive a more complex formula which takes into account the value of the input impedance of amplifier 18. This extension of my invention is considered apparent and it does not depart from the spirit of this invention, which in its most general form is the idea of loading the EKG electrodes with two different loads and determining from the reduction in EKG signal amplitude the inter-electrode impedance value. When the amplifier input impedance is much higher than $Z_T$, it can be assumed that there is no loading except for $Z_T$. The error which this introduces (since the amplifier input impedance can never be infinite) is generally not any greater than the error which also occurs as a result of the normal variations in the amplitude of EKG waveforms of the same patient taken at approximately the same time and under the same loading conditions. Because of these errors, the derived value for $Z_E$ can never be exact. The formula approximation is accurate enough, however, for most purposes.

In the preferred mode of operation, the value of the test impedance $Z_T$ is selected to have a predetermined value approximately the same as the maximum permitted inter-electrode impedance between electrodes 10 and 11. Preferably the value of impedance $Z_T$ should be the same as the maximum permitted inter-electrode impedance, but it may be within a range of perhaps an order of magnitude or more on each side of this value. Since the value of the test impedance $Z_T$ is known and the maximum permitted value of the inter-electrode impedance $Z_E$ is predetermined, the above formula will define a ratio $A_U/A_L$. The EKG amplitude ratio may then be monitored. When the amplitude ratio goes above this defined ratio, the inter-electrode impedance is higher than the predetermined maximum permitted value.

In order to determine whether the electrode impedances of electrodes 10 and 11 are within the range permitted, an operator starts recorder 20 and records at least one heart beat on the recorder 20 with the pushbutton not depressed and then depresses pushbutton 22 during at least one additional heart beat (or vice versa). The amplitudes of the EKG waveforms recorded under these two conditions are compared. If the EKG waveform taken while the pushbutton is depressed in half the amplitude of the EKG waveform taken while the pushbutton is not depressed, then the inter-electrode impedance is equal to $Z_T$, neglecting any loading effect of amplifier 18.

Figure 2:
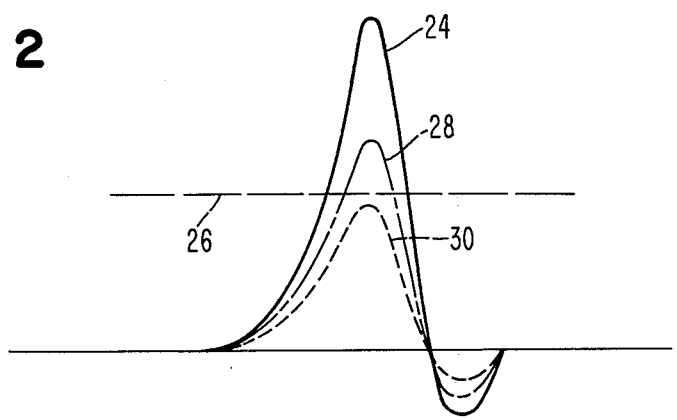
FIG. 2 shows EKG waveforms of different amplitude.

FIG. 2 illustrates the QRS complexes of three EKG waveforms superimposed for convenience. Waveform 24 was taken while pushbutton 22 was not depressed. Line 26 represents half the amplitude of the large amplitude positive wave (called the R wave). Waveforms 28 and 30 are two possible EKG waveforms which might be obtained from the same patient immediately prior to or following the recording of waveform 24 upon depressing pushbutton 22. The R wave of waveform 28 is above line 26, which means that the EKG electrode impedance was lower than $Z_T$ when this waveform was recorded. On the other hand, the R wave of waveform 30 is below line 26, which means that the EKG electrode impedance was higher than $Z_T$ when this waveform was recorded.

Figure 3:
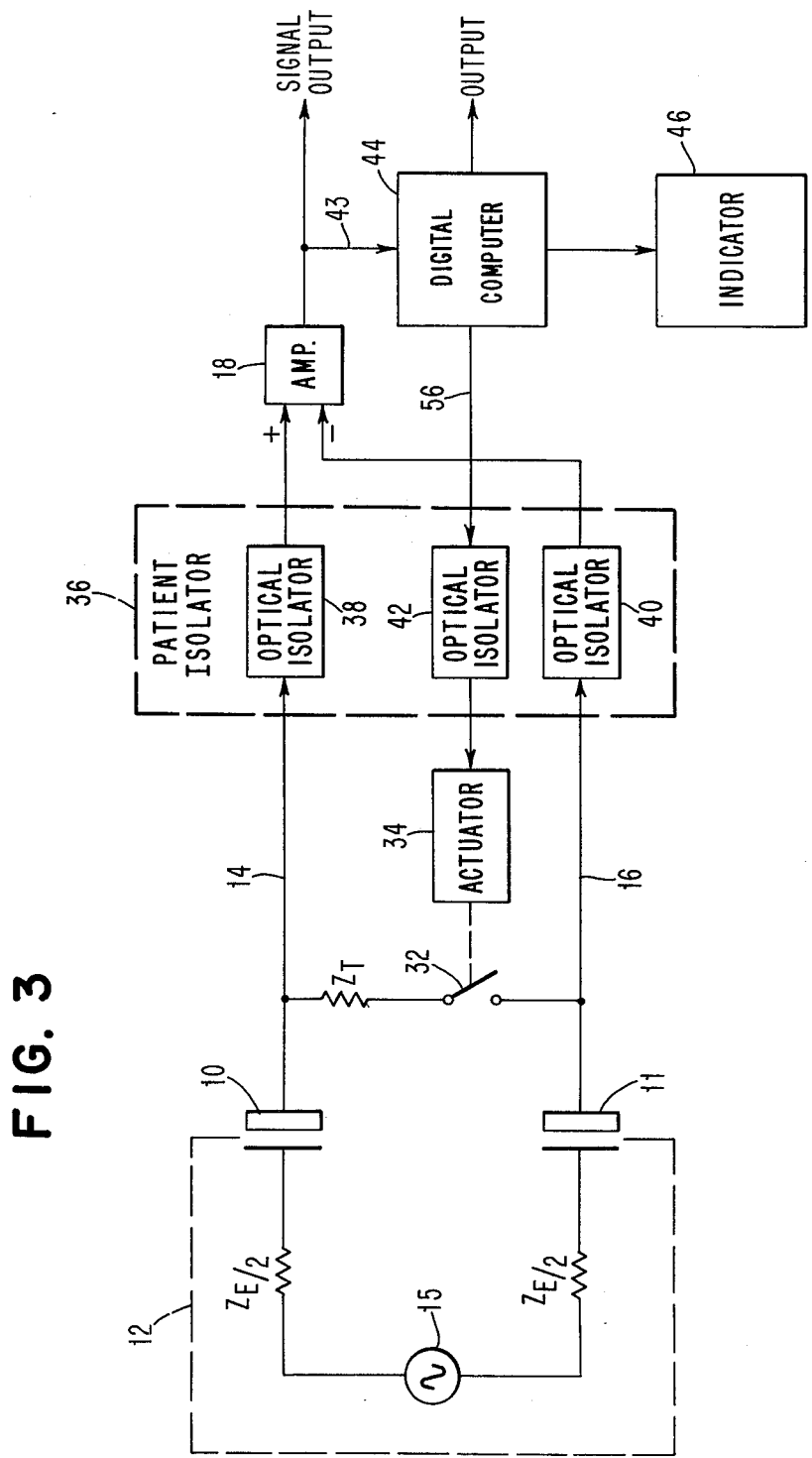
FIG. 3 is a block diagram of an automated embodiment of this invention.

FIG. 3 illustrates an automated embodiment of the invention. An equivalent circuit is represented here in place of the patient. $Z_E$ is the total inter-electrode impedance, which is represented here as two resistors, each of value $Z_E/2$. Voltage source 15 represents the source of EKG signals. In place of the pushbutton 22 is a switch 32, the position of which is controlled by actuator 34. EKG signals from the patient 12 as well as signals which control actuator 34 pass through a patient isolator circuit 36 which comprises electrical isolators 38, 40 and 42. These isolators are preferably optical isolators as shown. It is alternatively possible to control actuator 34 directly without going through an isolator 42 if the electrical switch 32 is in fact already suitably electrically isolated from the electrical drive of actuator 34. In FIG. 3 computer 44 automatically causes switch 32 to be closed and opened in a controlled manner. Switch 32 may be alternately opened and closed during successive heart beats or in accordance with any arbitrary schedule or plan. Either during or after an open and closed sequence of switch 32, computer 44 compares the amplitudes of the EKG waveforms obtained under alternate positions of switch 32. In one embodiment, when the loaded EKG waveform (switch 32 closed) has an amplitude lower than a predetermined percentage of the unloaded EKG waveform (switch 32 open), computer 44 causes an indication thereof to be displayed by indicator 46.

Figure 4:
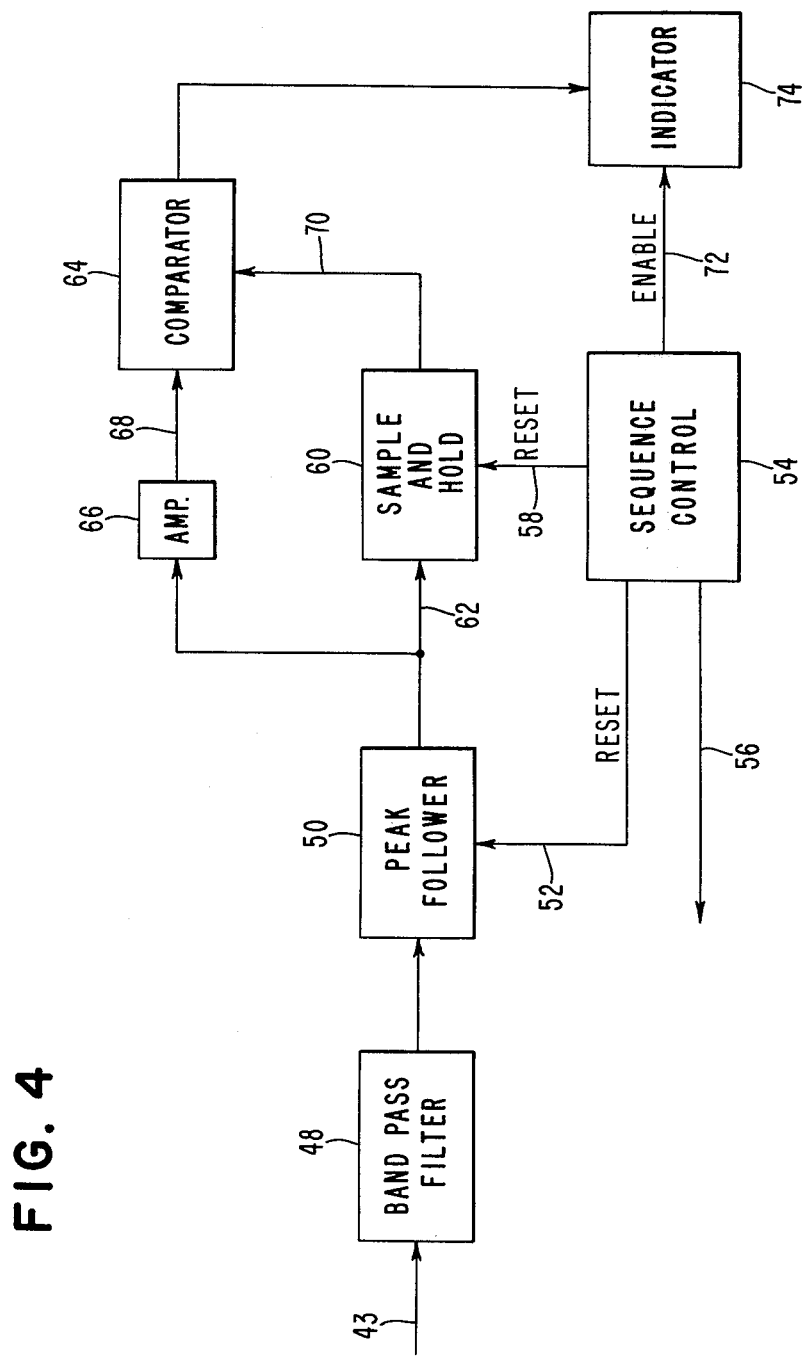
FIG. 4 is a functional block diagram illustrating one embodiment of the computer shown in FIG. 3.

FIG. 4 illustrates in further detail how computer 44 might function. Bandpass filter 48 removes from the signal received from the output of amplifier 18 those frequency components which are outside the range of frequency components of an EKG signal. The function of this filter is to eliminate signal components which are not part of the true EKG waveform but which could still affect subsequent signal level comparisons. The bandpass filter eliminates D.C. drift and removes high frequency artifact spikes, for example.

The output of the bandpass filter is presented to a peak follower 50, the function of which is to monitor the input signal thereto and hold (or store) the highest input amplitude value. The peak follower is reset via line 52 by sequence control 54. Sequence control circuit 54 also controls switch 32 (FIG. 3) via line 56. When the position of switch 32 is changed, peak follower 50 is also ordinarily reset by sequence control 54 so that it can then begin to find the maximum amplitude of the EKG signal with the switch 32 in the new position.

The peak follower should be finding the highest R-wave. In the presence of artifacts, a circuit which reliably does this is complex. However, there already are prior art circuits which do this and EKG analysis by digital computer inherently requires that the R-waves be located. Since this function is already performed by digital computer analysis programs, it is preferred that all of the data processing functions of this invention be implemented on a digital computer.

Figure 5:
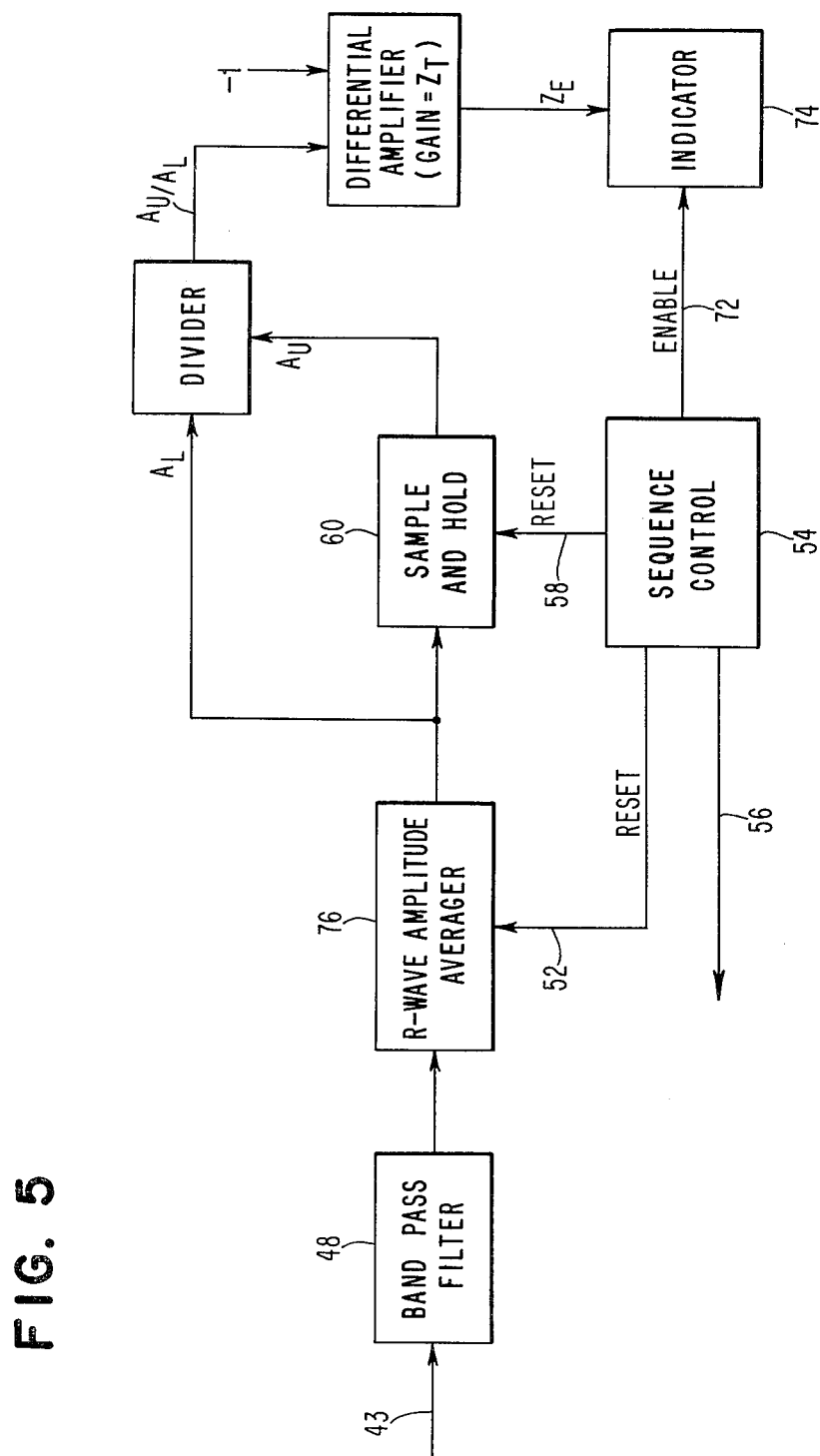
FIG. 5 is a functional block diagram illustrating another embodiment of the computer shown in FIG. 3.

It should further be apparent that the average amplitude of R-waves could also be readily computed by such a digital computer and computed average amplitude values used in place of maximum amplitude values. FIG. 5 illustrates such a direct substitution of an R-wave amplitude averager 76 in place of the peak 50. By using average values of R-wave amplitude the normal variations in such amplitude would also be expected to cause less of an error in the derived value of $Z_E$.

Returning now to FIG. 4, just before switch 32 is caused to be closed, a reset signal on line 58 from sequence control 54 causes sample and hold circuit 60 to receive via line 62 the highest amplitude value collected by peak follower 50 since the last reset thereof. This represents the amplitude of the unloaded EKG signal during the open position of switch 32.

After switch 32 has closed, peak follower 50 collects the highest amplitude value of the EKG signal during the loaded condition and presents it to comparator 64 via amplifier 66. The gain of amplifier 66 is adjusted to exactly compensate for the maximum permitted EKG amplitude reduction during the loading test. For example, if the maximum permitted reduction in amplitude is one-half, corresponding to an electrode impedance $A_E$ equal to the test impedance $Z_T$, then the gain of amplifier 66 will be two. If the loaded EKG signal then has an amplitude larger than one-half the unloaded EKG signal, the output of amplifier 66 presented via line 68 to comparator 64 will be greater than the value stored by the sample and hold circuit 60 (representing the amplitude of the unloaded EKG signal) which is simultaneously presented to comparator 64 via line 70. If the loaded EKG signal amplitude is less than the predetermined percentage of the unloaded EKG signal amplitude, the reverse will be true—the signal on line 70 will be larger than the signal on line 68.

When a sufficient time has lapsed since switch 32 has been closed so as to be sure that peak follower 50 has collected a maximum amplitude, sequence control 54 enables (via line 72) indicator 74 to display the results of the amplitude comparison. Computer 44 alternatively may directly calculate a value for $Z_E$ in accordance, for example, with the above described formula $$Z_E = Z_T(A_U/A_L - 1).$$

In FIG. 5 the functional block diagram of FIG. 4 has been modified in accordance with this formula, with the result that $Z_E$ now is directly computed for display by indicator 74.

The present invention has been described through use of function element representations. In practice, it is expected that all of these functions can and preferably will be implemented with a digital computer. There are many different medical monitoring and analysis systems in operation today which contain or use a digital computer and collect EKG signals. The functional requirements of the present invention may be conveniently and easily implemented in such systems through appropriate hardwire or software change in computer programming.

While the invention has been particularly shown and described with reference to a preferred embodiment thereof, it will be understood by those skilled in the art that the foregoing and other changes in form and details may be made therein without departing from the spirit and scope of the invention.

Having thus described my invention, what I claim as new, and desire to secure by Letters Patent is:

1. Inter-electrode impedance measuring apparatus for electrocardiography, comprising:
   two EKG electrodes;
   an impedance element $Z_T$;
   means for temporarily connecting said impedance element between said two EKG electrodes while said EKG electrodes are in position to pick up EKG signals from a subject;
   means for measuring both the amplitude $A_U$ of an EKG signal picked up by said EKG electrodes when said impedance element is not connected between said two EKG electrodes and the amplitude $A_L$ of an EKG signal picked up by said EKG electrodes when said impedance element is connected between said two EKG electrodes, the inter-electrode impedance $Z_E$ being related to $Z_T$, $A_U$ and $A_L$ at least to an approximation by the formula $$Z_E = Z_T(A_U/A_L - 1).$$

2. Apparatus as defined in claim 1 wherein said means for measuring has an input impedance which is much higher than $Z_T$.

3. Apparatus as defined in claim 1 wherein the impedance value of $Z_T$ may be varied.

4. Apparatus as defined in claim 1 where said means for temporarily connecting comprises a manually operatable switch and said means for measuring comprises means for displaying EKG waveforms.

5. Apparatus as defined in claim 4 wherein said means for displaying EKG waveforms comprises a strip chart recorder.

6. Apparatus as defined in claim 1 wherein said means for measuring comprises means for finding the amplitude of the largest R-wave in an EKG signal, the amplitude of the largest R-wave picked up when said impedance element is not connected between said two EKG electrodes being $A_U$ and the amplitude of the largest R-wave picked up when said impedance element is connected between said two EKG electrodes being $A_L$.

7. Apparatus as defined in claim 1 wherein said means for measuring comprises means for finding the average amplitude of the R-waves in an EKG signal; the average amplitude of the R-waves picked up when said impedance element is not connected between said two EKG electrodes being $A_U$ and the average amplitude of the R-waves picked up when said impedance element is connected between said two EKG electrodes being $A_L$.

8. Apparatus for aiding in the determination of tolerable inter-electrode impedance for electrocardiography, comprising:
two EKG electrodes;
an impedance element $Z_T$;
means for temporarily connecting said impedance element between said two EKG electrodes while said EKG electrodes are in position to pick up EKG signals from a subject;
means for measuring both the amplitude $A_U$ of an EKG signal picked up by said EKG electrodes when said impedance element is not connected between siad two EKG electrodes and the amplitude $A_L$ of an EKG signal picked up by said EKG electrodes when said impedance element is connected between said two EKG electrodes, the inter-electrode impedance $Z_E$ being related to $Z_T$, $A_U$ and $A_L$ at least to an approximation by the formula $$Z_E = Z_T(A_U/A_L - 1).$$

9. Apparatus as defined in claim 8 wherein $Z_T$ has a predetermined value related to the maximum permitted impedance value for $Z_E$, said predetermined value of $Z_T$ and said maximum desired impedance value for $Z_E$ determining in accordance with said formula a maximum permitted value for $A_U/A_L$.

10. Apparatus as defined in claim 9 and further comprising means for determining from the measured values for $A_U$ and $A_L$ whether the maximum permitted value for $A_U/A_L$ has been exceeded.

11. Apparatus as defined in claim 9 wherein said predetermined value of $Z_T$ is equal to the maximum permitted impedance value for $Z_E$, the maximum permitted ratio for $A_U/A_L$ thereby being equal to two.

12. Apparatus as defined in claim 11 and further comprising means for determining whether the measured value of $A_U$ is more than twice the measured value of $A_L$.

13. Apparatus as defined in claim 12 and further comprising means for alerting an operator that the maximum permitted value for $A_E$ has been exceeded when the measured value of $A_U$ is more than twice the measured value of $A_L$.

14. Apparatus as defined in claim 13 implemented with a digital computer.

15. Apparatus as defined in claim 9 wherein said means for measuring has an input impedance which is much higher than $Z_T$.

16. Apparatus as defined in claim 9 wherein said predetermined impedance value of $Z_T$ may be varied.

17. Apparatus as defined in claim 9 where said means for temporarily connecting comprises a manually operatable switch and said means for measuring comprises means for displaying EKG waveforms.

18. Apparatus as defined in claim 17 wherein said means for displaying EKG waveforms comprises a strip chart recorder.

19. Apparatus as defined in claim 9 wherein said means for measuring comprises means for finding the amplitude of the largest R-wave in an EKG signal, the amplitude of the largest R-wave picked up when said impedance element is not connected between said two EKG electrodes being $A_U$ and the amplitude of the largest R-wave picked up when said impedance element is connected between said two EKG electrodes being $A_L$.

20. Apparatus as defined in claim 9 wherein said means for measuring comprises means for finding the average amplitude of the R-waves in an EKG signal, the average amplitude of the R-waves picked up when said impedance element is not connected between said two EKG electrodes being $A_U$ and the average amplitude of the R-waves picked up when said impedance element is connected between said two EKG electrodes being $A_L$.

21. A method for measuring the impedance of EKG electrodes, comprising the steps of:
positioning two EKG electrodes on a subject which is generating EKG signals;
measuring the amplitude $A_U$ of the EKG signal picked up between the EKG electrodes;
connecting temporarily the two EKG electrodes together through an impedance $Z_T$ so as to reduce the amplitude of the EKG signl picked up between the EKG electrodes;
measuring the reduced amplitude $A_L$ of the EKG signal picked up between the impedance loaded EKG electrodes; and
deriving the impedance $Z_E$ between the EKG electrodes in accordance with the formula $$Z_E = Z_T(A_U/A_L - 1).$$

22. A method for determining whether the impedance of EKG electrodes is sufficiently low, comprising the steps of:
positioning two EKG electrodes on a subject which is generating EKG signals;
determining the amplitude of the EKG signal picked up between the EKG electrodes;
temporarily connecting the two EKG electrodes together through an impedance having a predetermined value related to the maximum permitted inter-electrode impedance;

determining the amplitude of the EKG signal picked up between the impedance shorted EKG electrodes; and determining whether the ratio between the amplitude of the EKG signal picked up between the impedance shorted EKG electrodes and the amplitude of the EKG signal picked up between the EKG electrodes when they are not impedance shorted is less than a predetermined value, the inter-electrode impedance being higher than permitted when said ratio is less than said predetermined value.

23. A method as defined in claim 22 wherein said predetermined value of said impedance is equal to the maximum permitted inter-electrode impedance and said ratio is one-half.

* * * * *